United States Patent
Charlot et al.

(10) Patent No.: US 11,322,230 B2
(45) Date of Patent: May 3, 2022

(54) SYSTEM AND METHOD FOR GENERATING AND IMPLEMENTING A STATELESS PATIENT HISTORY MODULE

(71) Applicant: Intelligent Medical Objects, Inc., Northbrook, IL (US)

(72) Inventors: Régis JP Charlot, Lake Bluff, IL (US); Frank Naeymi-Rad, Libertyville, IL (US); Ivana Naeymi-Rad, Chicago, IL (US)

(73) Assignee: Intelligent Medical Objects, Inc., Rosemont, IL (US)

( * ) Notice: Subject to any disclaimer, the term of this patent is extended or adjusted under 35 U.S.C. 154(b) by 152 days.

(21) Appl. No.: 13/887,117

(22) Filed: May 3, 2013

(65) Prior Publication Data
US 2014/0129258 A1    May 8, 2014

Related U.S. Application Data (60) Provisional application No. 61/722,778, filed on Nov. 5, 2012.

(51) Int. Cl.
*G16H 10/60* (2018.01)
(52) U.S. Cl.
CPC .................. *G16H 10/60* (2018.01)
(58) Field of Classification Search
CPC . G06Q 50/22–24; G06F 19/322; G16H 10/60
See application file for complete search history.

(56) References Cited

U.S. PATENT DOCUMENTS

| | | | |
|---|---|---|---|
| 5,799,268 A | 8/1998 | Boguraev |
| 5,930,788 A | 7/1999 | Wical |
| 6,055,540 A | 4/2000 | Snow |
| 6,101,515 A | 8/2000 | Wical et al. |
| 6,904,432 B2 | 6/2005 | Charlot et al. |
| 7,167,858 B2 | 1/2007 | Naeymi-Rad et al. |
| 7,496,593 B2 | 2/2009 | Gardner et al. |
| 7,536,387 B2 | 5/2009 | Charlot et al. |
| 7,693,917 B2 | 4/2010 | Charlot et al. |
| 7,711,671 B2 | 5/2010 | Meyers |
| 7,870,117 B1 | 1/2011 | Rennison |

(Continued)

OTHER PUBLICATIONS

"Semantic Web: Asking the Right Questions", Duch et al., Seventh International Conference on Information and Management Sciences, Urumchi, China, Aug. 12-19, 2008 entire document www.fizyka.umk.pl/ftp/pub/papers/kmk/08-SemWeb.pdf.

(Continued)

*Primary Examiner* — Sheetal R Paulson
(74) *Attorney, Agent, or Firm* — Quarles & Brady LLP (57) ABSTRACT

A system and method for receiving and processing patient medical information for integration into third party applications, including patient medical records, billing systems, and reporting systems. The method may be implemented as a software as a service application separate from the middle tier application server or other computer system implementing the third party application. In addition, the system may operate in a stateless environment in which the computer system running the SaaS application may not retain the patient medical information or data relating to a patient history interview state.

21 Claims, 6 Drawing Sheets

(56) References Cited

U.S. PATENT DOCUMENTS

| | | |
|---|---|---|
| 2003/0045782 A1 | 3/2003 | Iliff |
| 2004/0059599 A1* | 3/2004 | McIvor ................ G16H 10/20 705/2 |
| 2005/0240572 A1 | 10/2005 | Sung et al. |
| 2007/0179776 A1 | 8/2007 | Segond et al. |
| 2008/0046292 A1* | 2/2008 | Myers et al. ..................... 705/3 |
| 2008/0065452 A1 | 3/2008 | Naeymi-Rad et al. |
| 2009/0083231 A1 | 3/2009 | Eberholst et al. |
| 2009/0088607 A1* | 4/2009 | Muraca ............... A61B 5/0002 600/300 |
| 2009/0254572 A1 | 10/2009 | Redlich et al. |
| 2010/0169299 A1 | 7/2010 | Pollara |
| 2010/0262659 A1 | 10/2010 | Christiansen et al. |
| 2010/0324936 A1 | 12/2010 | Vishnubhatla et al. |
| 2011/0112866 A1 | 5/2011 | Gerrans |
| 2011/0184960 A1 | 7/2011 | Delpha et al. |
| 2011/0301982 A1 | 12/2011 | Green, Jr. et al. |
| 2012/0166525 A1 | 6/2012 | Dittrich |
| 2012/0179696 A1 | 7/2012 | Charlot et al. |
| 2013/0218598 A1* | 8/2013 | Aita et al. ........................ 705/3 |

OTHER PUBLICATIONS

"Social tagging overview (SharePoint Server 2010)" May 12, 2010 entire document http://technet.microsoft.com/en-us/library/ff608137.aspx.

Bronnert, et al., Problem-Centered Care Delivery, Journal of AHIMA 83, No. 7 (Jul. 2012): 30-35.

Notification of Transmittal of the International Search Report and Written Opinion dated Apr. 29, 2014, issued in International Application No. PCT/US2013/067822 (13 pages).

International Preliminary Report on Patentability, issued in PCT Application No. PCT/US2013/067822, dated May 5, 2015, 7 pages.

\* cited by examiner

SYSTEM AND METHOD FOR GENERATING AND IMPLEMENTING A STATELESS PATIENT HISTORY MODULE

This application claims the benefit of priority from U.S. provisional application 61/722,778, filed Nov. 5, 2012.

BACKGROUND

Obtaining as complete and accurate a patient history as possible is vital to provider care. Past techniques for gathering the data that form such a history have varied from having the patient fill out a hand-written form, e.g., during new patient registration, to more automated techniques, including performing natural language processing on physician or other user-entered information.

Care providers face several challenges in the process of data gathering. For example, the patient or user may be rushed before an appointment, the patient may not be comfortable truthfully and/or fully answering a question, the care provider may not have access to the user's history or family history in a short period of time. Each of these challenges may result in the care provider obtaining less than full or sufficient information to populate the patient's health record.

The information provided by the patient may be useful not just in diagnosing or treating the patient, but also in documenting the care event, as well as in providing for billing, analyzing results, or serving as a basis for later research and/or analysis.

While this information may be useful for various purposes, practical concerns exist that may complicate the processes of data collection and processing. Medical information may be subject to various privacy laws that place restrictions or requirements on what can be done with or to the data. For example, in the United States, the Health Insurance Portability and Accountability Act (HIPAA) restricts who can access and edit data and further requires that audit trails be maintained to determine when, how, and by whom data has been changed.

In addition, as more electronic health records are established and maintained, a system that is configured to interact with those records is necessary to transmit information to one or more computer networks, using established health information communication standards, and ontology that may be recognized by receiving entities.

What are needed are a system and method that address the issues presented above.

BRIEF SUMMARY

In one aspect, a method for receiving and processing patient medical information, may include the steps of (1) transmitting data comprising a question and possible answers designed to obtain medical information to an application server; (2) receiving data comprising a response to the questions from the application server; (3) gathering and analyzing the response data including applying a response clinical terminology code(s) supporting the answer; and (4) transmitting the codified response data to the application server. The code values may relate to one or more reference terminologies, administrative codes sets, or clinical code sets, although they preferably include at least clinical interface terminology codes.

Between steps (1) and (2), the application server may format the question-related data, transmit the formatted data to an end user computer system, and receive a response to the question from the end user computer system. In addition, the analyzing step may include determining a next question to transmit to the application server and then repeating steps (1) through (4) for the next question. Moreover, between steps (3) and (4), the codified response data may be formatted for integration with an electronic health record.

The method may be implemented in a stateless fashion, where a computer system may perform the analyzing and codifying step, and that computer system does not store a state of the questions and answers. Instead, an interview state storage and management device located on a different application server and in communication with the stateless computer system via an Internet or intranet connection and/or an end user's computer (e.g., the user's browser) may be responsible for maintaining the interview history state.

In another aspect, a method for receiving and processing patient medical information having a state may include the steps of: transmitting data comprising a question designed to obtain medical information from a first computer system to a second computer system; receiving data comprising a response to the questions from the second computer system; analyzing, by the first computer system, the response data and codifying the response data with one or more code values; updating the state of the medical information; transmitting the codified response data and the updated state to the second computer system; and not retaining the state of the medical information on the first computer system.

The method also may include the step of retaining the state on the second computer system or on a third computer system, the third computer system comprising the system initially transmitting the data comprising a response to the questions.

Data in the receiving step may be in an XML format. It then may be formatted, after being analyzed, for integration with an electronic health record, and the formatting may require configuring the data according to a Continuity of Care Document or a Clinical Document Architecture standard.

In still another aspect, a system for receiving and processing patient medical information may include a first computer system configured to transmit question data, receive answer data, codify the answer data, and transmit the answer data. The first computer system may not retain a state of the question data, which instead may be maintained on an application server tier and/or on an end user's system.

The first computer system may include a software as a service application configured to communicate with a middle tier application server and to transmit the question data and answer data. That application may be configured to analyze answer data and determine a next question to transmit to the middle tier application server. In addition, the system may include, for each answer, a data file including clinical interface terminology codes in communication with the application in order to permit codification of the answer data.

These and other features and advantages are described in the following description, with reference to the accompanying drawings.

DETAILED DESCRIPTION

A system 10 and process for receiving and processing patient medical information, e.g., medical history information, providing an output that is consumable as part of an electronic health record ("EHR"), and delivering content fit for meaningful use needs for clinical vendor partners is described herein. In one aspect, the information may be retrieved as part of a patient medical history interview prior to physician encounter. In this manner, the patient can provide the requested information on his or her own timetable and can spend additional time obtaining answers to questions for which those answers might not be readily available.

The interactive computer-based patient dialogue and data management system and method described below may lead to: enhanced communication between patient and care provider, reduce healthcare costs, and supplementary codified history for meaningful use.

Software as a Service Aspect of System

Instead of centralized hosting of software to execute the process, system 10 may make this clinical interview content and workflow available through use of a software as a service ("SaaS") Patient History Interview Module. This module may be hosted on a remote server 12, e.g., a cloud computing-based server, which may allow the module to execute the process for multiple independent recipients, e.g., multiple hospitals, doctors' offices, or other health care providers. Remote server 12 may drive the capture of information (local or cloud hosting), and may be agnostic to the integration platform.

Figure 1:
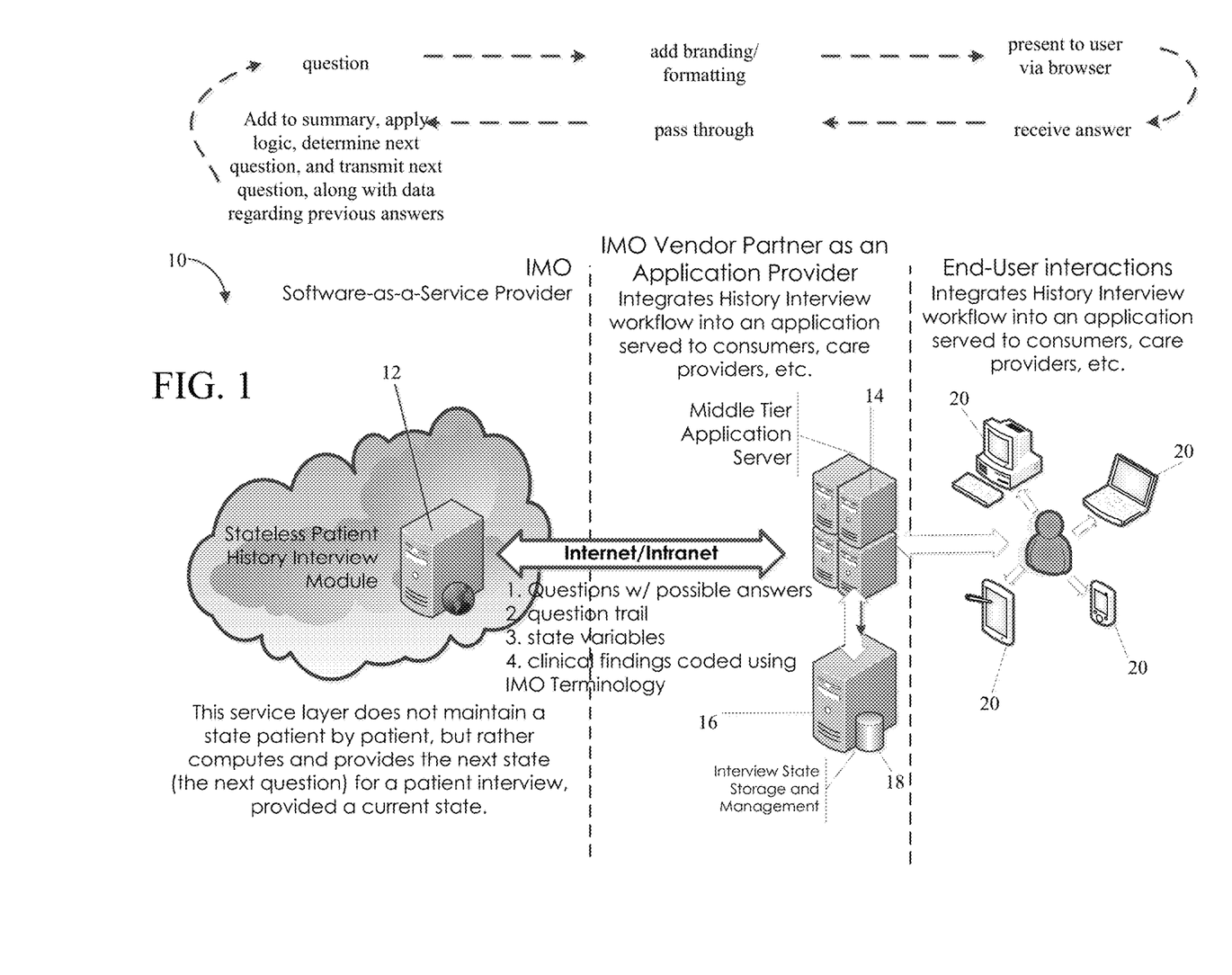
FIG. 1 is a schematic of a system that includes the interaction between a stateless electronic patient history record engine, a storage and management device, and multiple end users that can access one or more vendor partner applications.

In this environment, server 12 may communicate with one or more middle tier application servers 14, which may store the relevant patient information, host the patient's EHR, and communicate directly with end users. In one embodiment, as seen in FIG. 1, a middle tier application server 14 may include or be in communication with an interview state and storage management device 16, which may include a database 18. Database 18 may be configured to receive, store, update, and transmit patient history information, as well as interview state information.

Server may require the overall state for a history section and an answer to the current question in order to determine the next question to transmit to the user. Interview state can be served anywhere, although preferably state is not stored on server 12. Instead, state preferably is maintained in at least one of application server 14 or end-user device 20, e.g., on a browser as a session variable.

In view of this configuration, the patient history module preferably also may be a stateless service, as discussed in greater detail below.

The information retrieval process may be automated, e.g., the system may include hardware or software containing instructions to cause a processor on one or more computers, e.g., 12, 14, 16, 20 to implement one or more steps of the process.

In addition to receiving patient information, system 10 also may integrate terminology into the patient data file in order to deliver content fitting meaningful use needs for one or more additional or external services, such as clinical vendor partners (billing, reporting, etc.).

Patient history information may be received from the patient or another end user via inputs transmitted from end-user devices 20. Specifically, patient interview history module on server 12 may include or be operatively coupled with a patient data broker—a health information exchange or a health organization EHR—which may provide questions to a patient in order to retrieve information about the patient.

Interface state storage and management module 16 may be in communication with one or more end user devices 20, resulting in system integration with vendor partners across multiple platforms. Questions are presented to a user on one or more end-user devices 20, e.g., personal computers, patient kiosk computers, cellular devices, tablets, or other computing devices, and may permit the patient history interview module ultimately to receive the user's responses to those questions. In one embodiment, data may be transmitted and displayed to end user devices 20 or received from end user devices 20 via a traditional Internet browser interface.

The system and method may be part of an EHR/PHR system or may integrate with the EHR/PHR software in order to report coding historical information back to EHR/PHR. As discussed in greater detail below, the captured information may be encoded consistent with a standard usable to extract the patient data into a form usable in the EHR. Examples of these data standards include Continuity of Care Document and Clinical Document Architecture standards, which preferably results in a seamless EHR integration of patient data.

The system may receive and store the patient's responses, as well as the context in which those responses are given. As discussed above, storage preferably occurs at a middle tier level, such as in middle tier application server 14 and/or interview state and storage management device 16, or at end user device 20 level.

In addition, the engine may provide a new question or set of questions to obtain additional information, reach clinical confidence, and/or determine appropriateness. The process of asking for and obtaining answers to patient history questions may comprise a patient history collection workflow.

Figure 2:
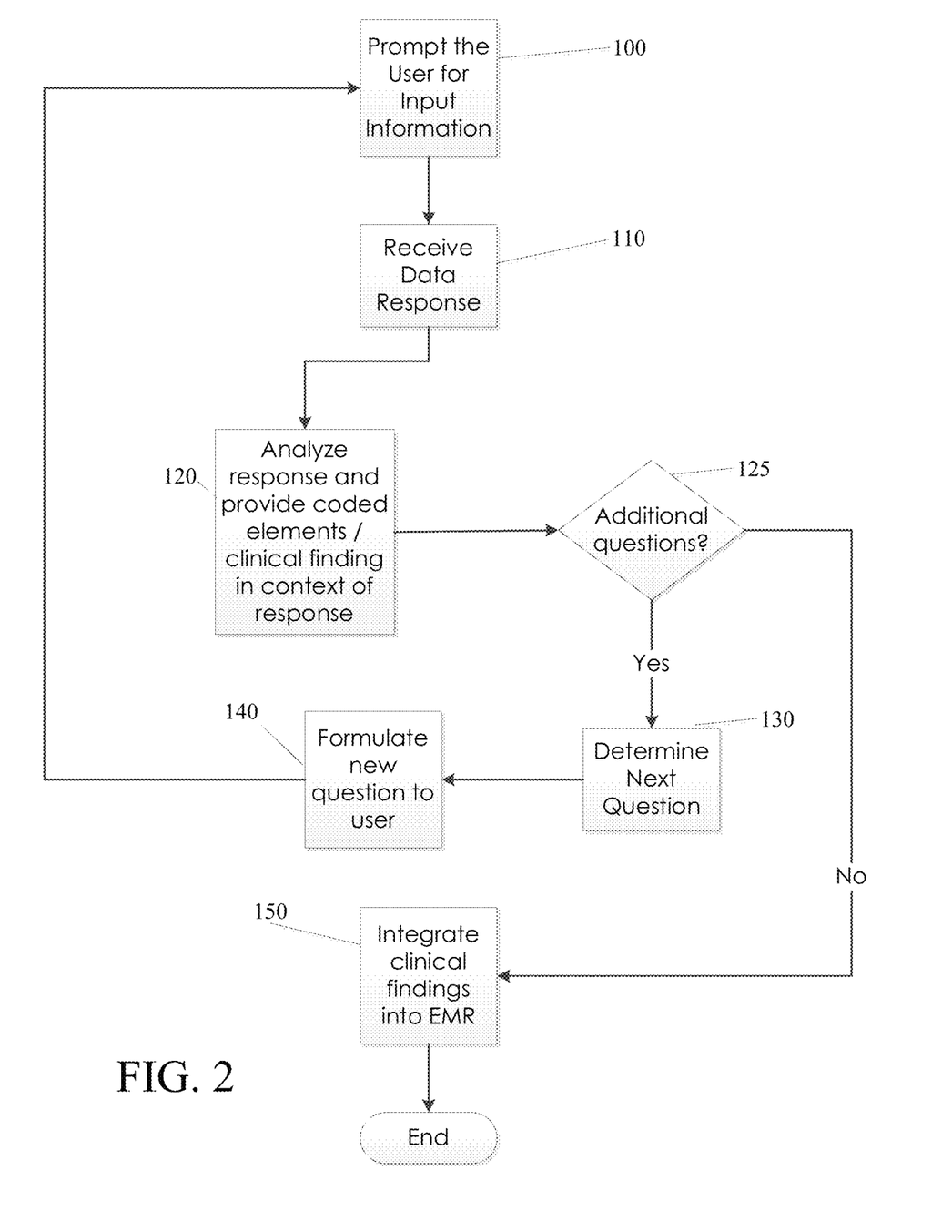
FIG. 2 is one example of a process flow for data in a stateless patient history interview system.

FIG. 2 illustrates one example of this collection workflow. At step 100, the system may prompt the user for input information by posing one or more questions to the user.

Questions may be ordered in such a way as to give context to responses, e.g., grouping questions about allergies together, asking about symptoms, current medications, etc. These groups further may be divided into subgroups. For example, the system may alert the user that the following questions relate to allergies and then alert the user that a first set of questions are about food allergies, followed by an alert that questions are about medication allergies, etc.

Questions also may be of one or several types, e.g.: a) Yes, No, Uncertain, Don't Understand, I'd Rather Not Answer; b) Free Text, and/or c) Multiple Choice (multi and single selection). The content and categorization of questions may be predetermined in order to provide a consistent experience to multiple users (although the actual questions asked may differ depending on the responses received from the users).

At step 110, the system may receive the user's response to a question and proceed to analyze that response by providing coded elements and/or clinical findings in the context of the response, as at step 120.

Analysis of the user's responses may lead to one or more different actions being taken. For example, the system may proceed to determine if additional questions remain at step 125. If the answer is yes, it may determine the next question at step 130, formulate that question at step 140, and loop to prompt the user for a response, as at step 100. If the answer is no, the user's responses and related clinical findings may be integrated into the EHR, as at step 150.

The determining step of 130 may be implemented in multiple ways. For example, using the context in which the questions are asked, confidence may be established, appropriateness may be computed, and a new set of questions may be formulated based on the user's responses. In one embodiment, the progression of questions may be predetermined such that the system may be pre-programmed to know which question to ask next, given the user's answer to the current question.

Alternatively, the system may ask a sequence of questions and not deviate from that sequence, regardless of the patient's responses, such that step 130 may include selecting the next question from a predetermined list.

In still another aspect, the system may include different types of questionnaires depending upon the circumstances, in order to collect more accurate, more useful information. For example, a patient seeking health maintenance may receive a first questionnaire or series of questions, while a patient seeking disease management may receive a second questionnaire or series of questions.

Returning to step 120, analysis of the patient's answers may include displaying a summary of the patient's responses to the patient so that the patient may be able to review and edit his or her responses. This displaying sub-step may occur after the system receives the patient's answers or after each question section.

The patient history module also may transmit the patient's responses to a computer system viewable by the health care provider.

Returning to FIG. 2, at analyzing step 120, responses may be received or converted into a structured, machine-readable and extractable format, e.g., XML. In one aspect, this data format may be the same one used to integrate the data into the EHR. Preferably, however, it may be a different, simpler format such that the ultimate formatting may not occur until the end of the questionnaire or the end of a set of questions, which may reduce processing time and the demand on system resources. In order to determine what other questions, if any, should be posed to the user, system 10 may codify the data obtained as part of these responses with appropriate codes, as at step 140.

Staying with step 120, portions of responses may be analyzed and tagged with relevant concepts, descriptions, and/or codes. Codes may correspond to administrative code sets, clinical code sets, and/or reference terminology code sets, in order to provide enhanced functionality for the captured data. Alternatively, codes may correspond to an interface terminology that, in turn, may link to one or more of these other code sets. In one embodiment, codifying may include adding or linking terminology references (e.g., IMO® ProblemIT, IMO® ProcedureIT clinical terminologies) to answer data Linking with terminology references may provide support for later intelligent reporting and data mining. For example, the coding may allow captured data to carry meaningful use information (including both stages 1 and 2).

Additional information regarding reference terminologies may be found in the commonly-assigned U.S. application Ser. No. 13/004,128, filed Jan. 11, 2011 and titled "System and Process for Concept Tagging and Content Retrieval," and additional information regarding linking or tagging interface terminologies with other code sets or terminologies may be found in the commonly-assigned U.S. application Ser. No. 13/660,512, filed Oct. 25, 2012 and titled "Method and System for Concept-Based Terminology Management," the contents of both which are incorporated herein by reference.

Each response may generate one or multiple concept tags, which may reside in the same or different domains. For example, in a "medication" section of the interview, the user may be asked if he or she has ever had an allergic or other adverse reaction to the pain medicine known as acetaminophen. Upon receiving a user answer of "yes," the response may be tagged with a tag relating to the concept "acetaminophen" in a "medication history" history sub-domain and also may be tagged with a tag relating to the concept "acetaminophen" in a "patient medication list" medication sub-domain.

Each tag includes information sufficient to determine the identity and location of the concept to which it applies, e.g., a unique numerical identifier and/or other identifying information. For example, concepts may reside within multiple domains (and, potentially, subdomains) and may have identifiers that are unique across those domains and sub-domains, so that the identifier itself may suffice to determine the concept.

In another embodiment, concepts and their identifiers may be unique within a domain or subdomain but not across multiple domains. For example, "acetaminophen" may be a concept used in both a patient medication list domain and a patient medication history domain and may have the same identifier in each case. (In that case, there may be a common domain to each of these instances, e.g., a dictionary domain, which stores each concept and its identifier code.) In that embodiment, the identifying information also may include an indication of the domain and, if relevant, subdomain, in order to determine accurately how the tag applies.

In still another embodiment, the "medication—acetaminophen" concept and the "patient medication history—acetaminophen" concept may be considered separate concepts that, by definition, may include distinct identifiers.

The output file generated by receiving and analyzing the user's responses may be in a machine-readable format, such as XML. Entries in the file for each question may be arranged according to the section to which each question pertains. Within each section, the entries may include a list of: the relevant code that has been ascribed to a response, and indication of the domain to which the response relates and an identifier of the question being answered, a description of the code and/or a description, which may be a semantic, alternative way to represent the concept that was used. The text also may include a text-based narrative or description of the section from which the data originated.

At step 150, the responses then may be used to generate a textual output with coded data, which then may be integrated into an EHR. As discussed above, this integration may require conversion of the output into a CCD, CDA, or other standard usable by the EHR. This output may be used for reporting and other uses. The data in each answer may generate one or more new findings that may be imported into the patient's electronic record.

FIG. 2 illustrates one data flow example, in which the reporting and integration are performed after the last question has been asked.

Figure 2A:
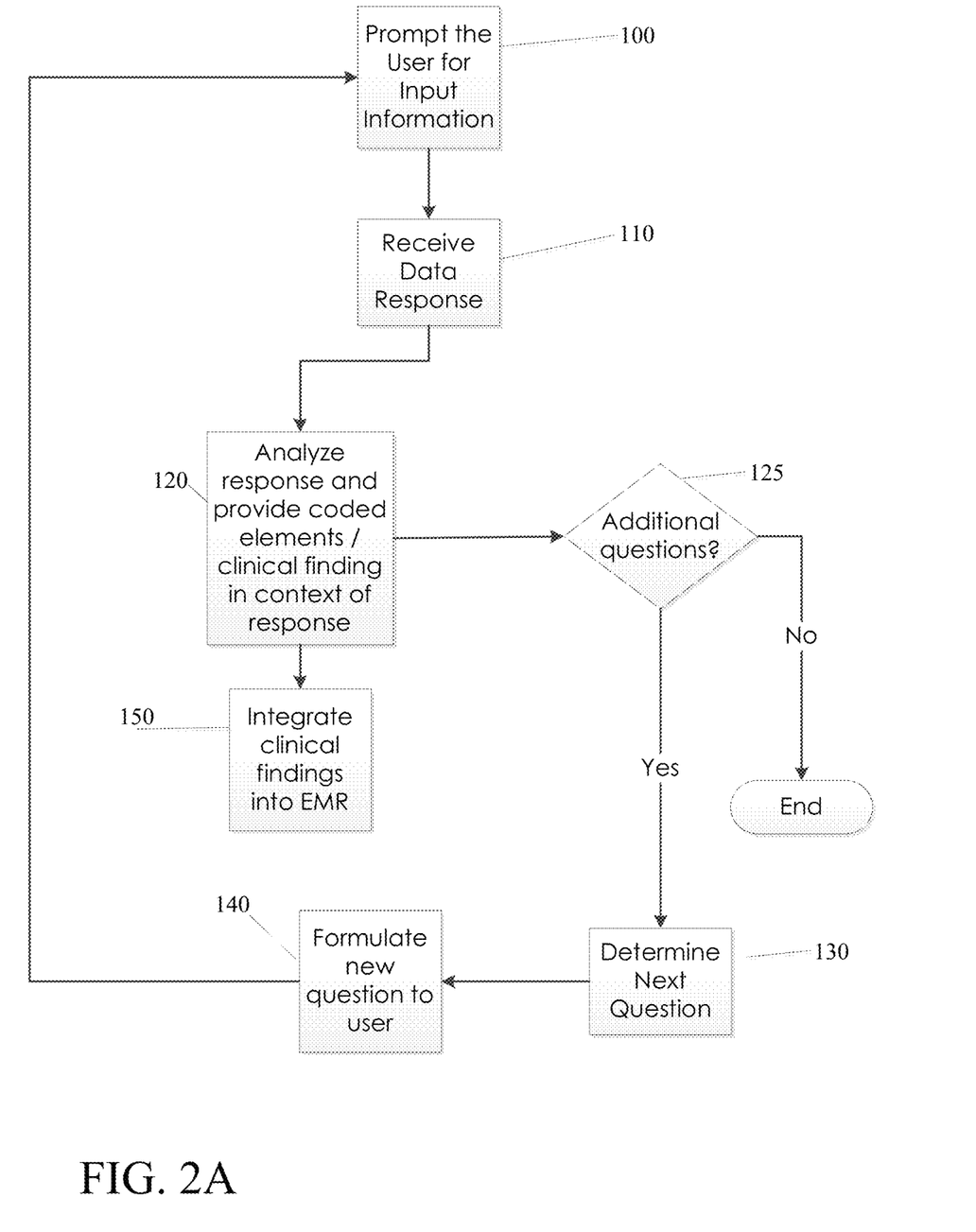
FIG. 2a is a second example of a process flow for data in a stateless patient history interview system.

Alternatively, it may be desirable to report and integrate findings at earlier points, such as in the data flow example of FIG. 2A. That figure illustrates a work flow that proceeds through step 120 in the same manner as in FIG. 2. After analyzing each response at step 120, the system may determine whether additional questions remain at step 125. Concurrently, i.e., after each question, the system also may implement step 150, integrating the findings into the EHR.

Figure 2B:
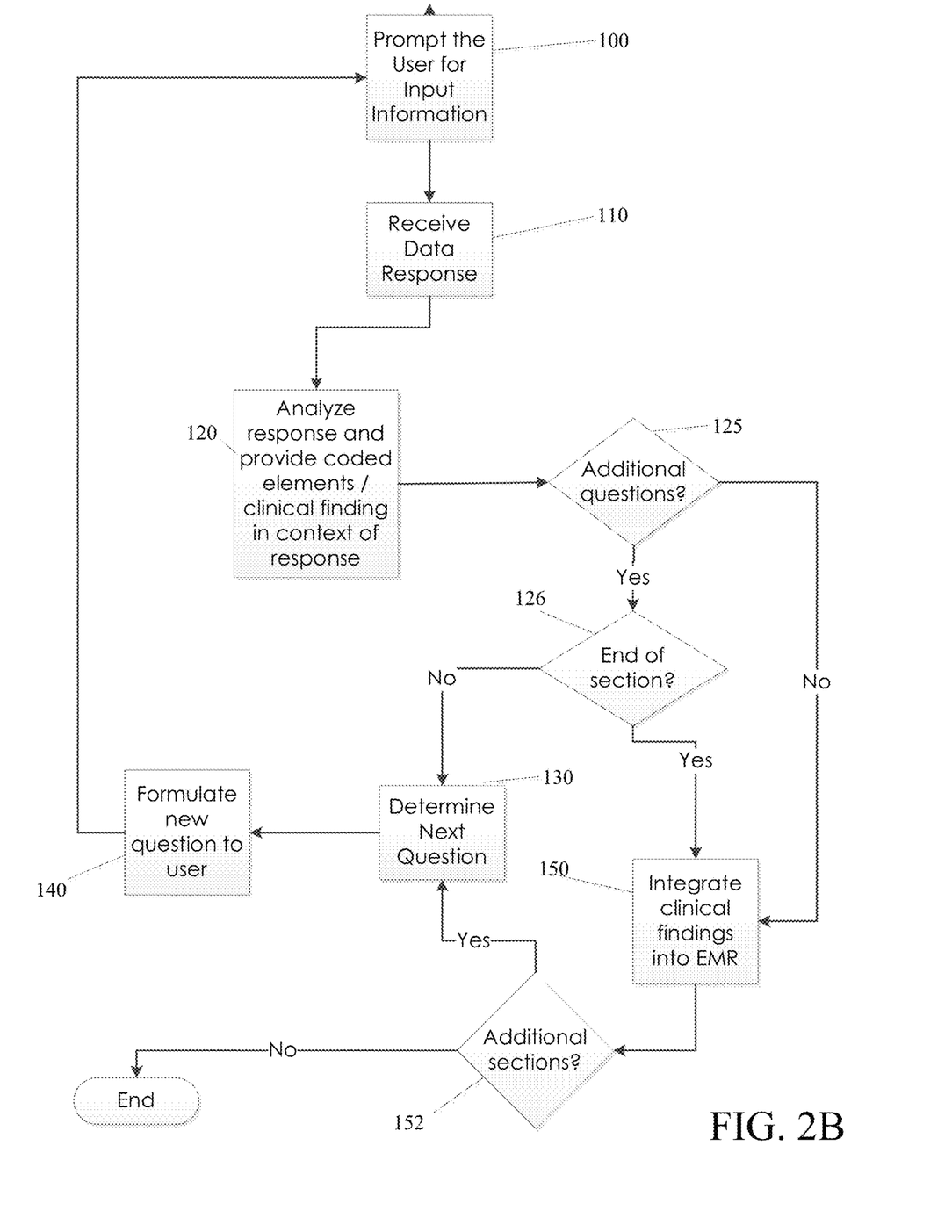
FIG. 2b is a third example of a process flow for data in a stateless patient history interview system.
Figure 3:
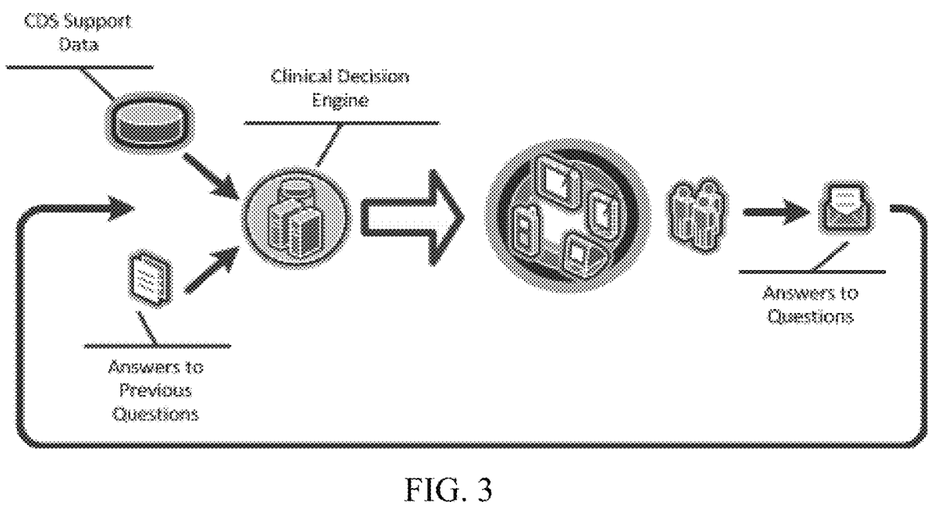
FIG. 3 is a second schematic of data collection, analysis, and output workflow in a patient history interview module.

FIG. 2B shows a further data flow example in which integration occurs more frequently than in FIG. 2 but less frequently than in FIG. 2A, i.e., after each section of questions. In this example, after it is determined in step 125 that there are additional questions, the system may determine whether it has reached the end of a section or not, as at step 126. If not, the system proceeds to ask the next question at step 130, whereas it proceeds to integrating step 150 if the end of the section is reached. When those records have been integrated, the system then may check to see whether there are additional questions sections at step 152, e.g., the system may have completed a "history" section of questions and still may need to ask questions relating to "medication," "allergies," etc. If additional sections remain, the system may revert to step 130 in order to determine what the next question to present to the user is.

In each of the work flows described above, the clinical finding created in step 150 may be established using the workflow or DSS engine, which may implemented as software executed by a processor that is integral within or operatively coupled to computer 12. A DSS is the representation of organized content using coded terminology. The DSS may rely on logic and/or knowledge, which may be both textual content and data supporting the DSS process. In addition, as seen in FIG. 4, it may be an iterative process, where a set of questions may lead to another set of questions, before a decision can be made.

This iterative process may be accomplished by dividing the questions into a series of subsections, where each subsection may be a series of branches in a decision tree; some answers may lead to the same next question, i.e., the next question is the only child for the parent question, while others may have multiple possible children questions. The system may proceed until it reaches the last question in a branch of the tree before applying the appropriate code tagging. The system then may proceed down a second branch within that tree, repeating the process until questions for the subsection are complete.

Figure 4:
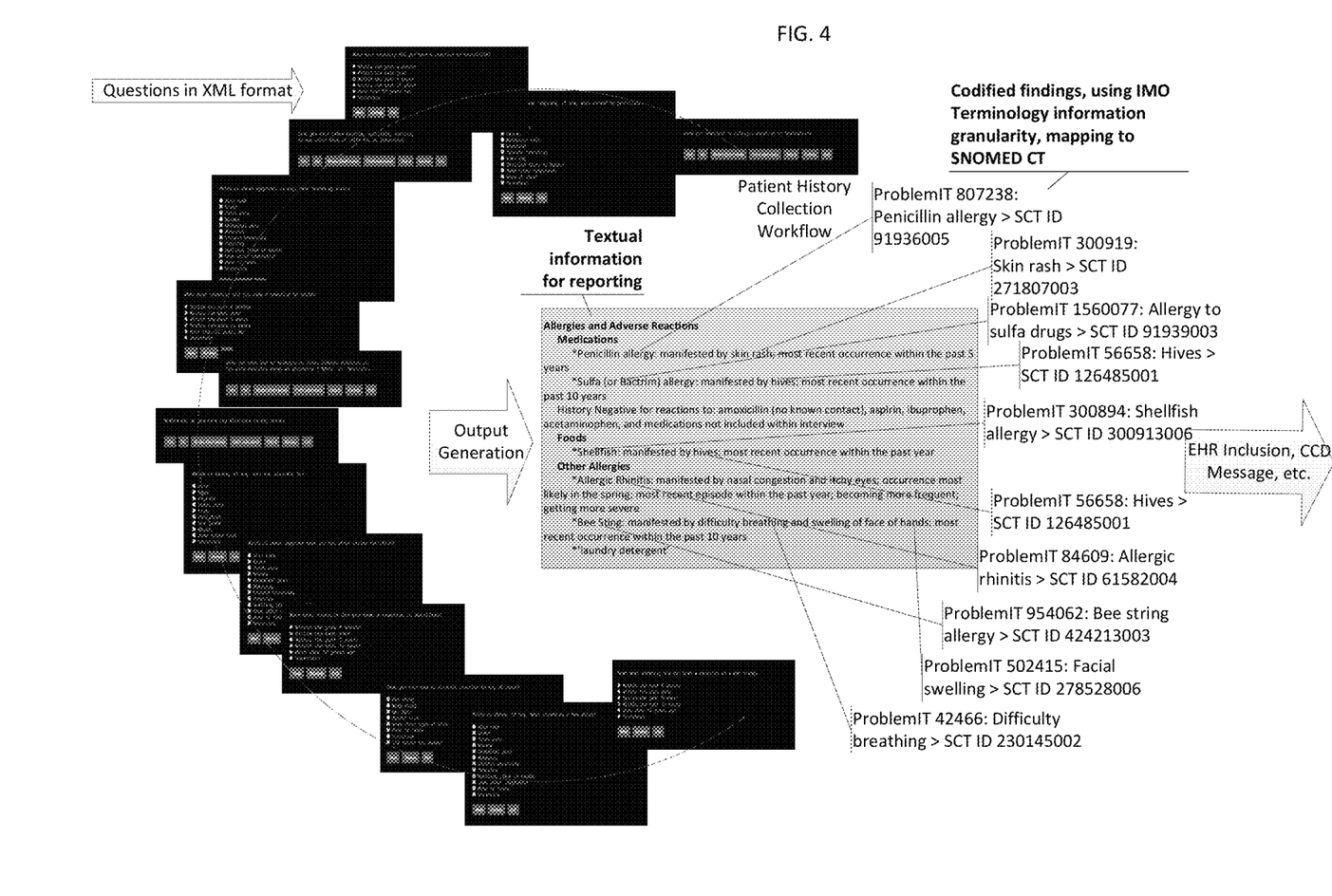
FIG. 4 is a schematic of the iterative process behind decision support services (DSS).
Figure 5:
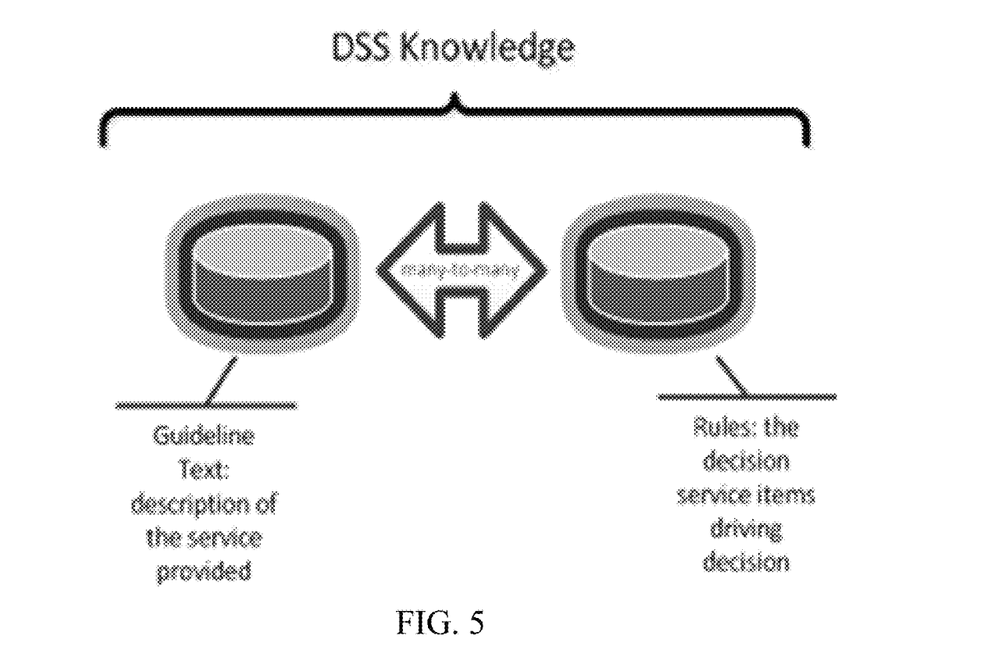
FIG. 5 is a visualization of the many-to-many relationship between guidelines and rules as components of a DSS knowledge base.

As seen in FIG. 4, the workflow/DSS engine may be integral within or operatively coupled to computer 12 and may be a stateless device in communication with an interface state storage and management module 16, e.g., via a middle tier application server 14. The workflow/DSS engine may be in two-way communication with middle tier server 14 via intranet, Internet, WAN, LAN, or any other form of communication. Middle tier application server 14 may integrate interview workflow data into an application that is served to consumers, care providers, etc. For example, application server 14 may receive question and possible answer data from workflow/DSS engine and add relevant branding, formatting, etc., in order to present the data to the user in a desired format.

In short, among other tasks, middle tier server 14 may receive a communication (request) from user computer 20, the communication including one or more answers to one or more questions. Middle tier server 14 then may store those answers in a database, such as database 18. Middle tier server 14 also may communicate with workflow/DSS engine to receive other information, e.g., decision information and/or next question information, before sending data back to client device 20.

From there, the tagged output may be exported to one or more additional modules and/or external systems, e.g., for EHR inclusion, etc., as at step 150. As discussed above, this step may include reformatting the data from the format in which it is captured into a format or standard usable by the EHR, such as the Continuity of Care Document (CCD) standard. In the event of exportation to an EHR, and as a result of the tagging to the answers that occurred previously, entries in that record may be codified and further may express clinical intent, providing a more accurate, more robust record for the practitioner. Those entries also may be formatted and/or displayed in a manner that either is similar to how the practitioner views EHR records or in a format that provides similar information to the practitioner as other EHR records. Preferably, middle tier server 14 is responsible for this formatting, although it may be carried out by one or more other computer systems.

Stateless Aspect of System

In one embodiment, server 12 may store each end user's answer to each question. Preferably, however, the system may not retain any answer data but instead may build an answer list that gets passed back and forth between server 12 and middle tier application server or servers 14, relying on interview state storage and management device 16 and/or related database 18, which are operatively coupled to middle tier server 14, and/or end user's computer 20, to provide such data storage and maintenance.

In one embodiment, each question yields its own answer list, such that each answer may be codified and delivered to middle tier server 14 for integration into the EHR.

In another embodiment, the answer list data file may continue to be passed between server 12, middle tier application server 14, and/or end user devices 20, and each successive answer may be appended to the end or otherwise added to the list.

In one aspect, data may be transferred in a machine readable format such as XML, and this XML file may be revised or rewritten with each new answer. Within the XML file, data may be arranged as a list or array. For example, each question presented to the user may include a frame or sequence number, and the list or array may take the form: [frame/sequence_number: answer choice][next_frame/sequence_number: answer choice] [etc.]. As discussed above, the order of questions may be based at least in part on the user's responses. As such, the frame/sequence numbers for successive elements in the list may not necessarily be sequential.

In addition, certain questions may include multiple answers, e.g., a patient listing relevant symptoms or allergies may have multiple symptoms or multiple allergies. As such, the "answer choice" field may comprise multiple entries.

In some cases, such as in the case of a free text entry, the entries in the answer choice field may be understandable when the list is read in the abstract. Alternatively, the answers may correlate to identifiers representing the possible choices displayed to the user, e.g., "1" or "A" may correlate to the first possible choice, "2" or "B" to the second possible choice, etc. In that way, the combination of the frame/sequence identifier and the answer identifier may be necessary to determine the substance of the user's response.

In previous data collection systems, questions were asked and data was entered. The system then called one or more functions, using the entered data as variables for the functions. The results of the function call then may have been saved in the EHR.

In contrast, the current system may separate the processor responsible for the data analysis from the subsystems storing and hosting the application that is served to end users. The processor may be within computer operating stateless module 12, which may be a web service or other remote service accessed by middle tier server 14.

As discussed herein, the "state" of the interview process may include data relating to: (1) the questions answered/the user's answers to those questions; (2) data necessary to establish the codification or tagging of those answers; and/or (3) summary information, which may be created from previous answers, sufficient to provide a textual representation to the user.

In order to maintain a state of the interview process, the system may push that responsibility to either the client application server 14, or to the end user's machine 20. If end user accesses the system via a thin client, accessible with an Internet browser, the browser may be tasked with maintaining state. This may be done, e.g., by storing the data in one or more cookies or one or more temporary session variables. In a thin client implementation, the state may be released every time an answer is provided to the middle tier server, and a new state may be obtained when the middle tier server provides the next question.

Alternatively, this "thin" implementation may be replaced with a thick client implementation on the user's computer 20, e.g., a separate, dedicated application installed on that computer, and the state may be maintained more permanently in memory. Permanence in this sense is contrasted with the operation of session variables, which may be deleted when the browser is closed, or with cookies, which may be provided with a specific time for deletion. In the thick client implementation, data representing the state still may be deleted or modified often, such as after each new question is answered, while still being considered as having more permanence.

The stateless engine/module/service layer may not maintain a state on a patient-by-patient basis. Instead of maintaining and recording the state of the data at each stage throughout the data gathering process, stateless history module 12 may be concerned with the current question or answer. It may compute and provide the next state, i.e., the next question, for a patient interview, given a current state.

Data transmitted to and received from the stateless history module may not be attributable directly to a patient, i.e., the module does not receive any patient identifying data or retain any patient history information. As such, the constraints imposed by HIPAA compliance, including the recordkeeping and audit history requirements may not apply, which may result in stateless history module 12 being significantly more flexible than medical records systems that retain that information.

While stateless history module 12 may not store any identifying patient data, it still may be necessary to ensure that data is transferred to and from the proper end user computer 20 over the course of the interview. Between computer 20 and middle tier server 14, this may be accomplished by authenticating the end user, e.g., via a username/password entry, and establishing an identity for the user's session, e.g., by generating a session ID, an application ID, an encryption key, etc. Alternatively, it may be possible to use the IP address associated with computer 20, although this option may be less preferable, as it may be possible to "spoof" the IP address of another user to access their information. Once the user is verified, the system may be configured to trust that all answers that it receives from that user during that session pertain to that user.

The system may be configured to time out or require reauthentication if it has reason to doubt that the same user still is accessing system 10. This may occur, e.g., if a predetermined amount of time has elapsed since the user last submitted an answer or if the user closes the browser session.

Further authentication may be required between middle tier server 14 and interview module 12. This may be accomplished by providing a key or ID along with the data transferred from one system to the other. In one embodiment, this may be the same key or ID used to transmit data between middle tier server 14 and end user computer 20. Alternatively, a separate key may be generated and used. Since interview module 12 does not care about the identity of the end user 20 but instead is being used to analyze data and return a result, it may suffice to apply a transaction ID to any request from the middle tier server and then maintain that transaction ID when transmitting a response from the interview module. Alternatively, a separate transaction ID may be applied for each call to/from the interview module, i.e., each time a new answer is sent from the middle tier to the interview module or a question is sent from the interview module to the middle tier server.

In addition, because SaaS patient history interview module 12 may not store all the relevant data but instead is an application that repeatedly is called on demand, the XML or other data file transferred to and from that module with every question and answer may be small, e.g., a few kilobytes in size. As such, data transfer to and from interview module 12 may consume few system resources, allowing for large scale scalability of system. For example a single server host could handle several hundreds or thousands of requests at a time. Conversely, due to the stateless nature of a request, several hosts could handle incoming requests concurrently, resulting in requests from the same patient being handled by different hosts along the life of the patient interview. For example, a first host server may analyze the user's response to the first question, and a second host may analyze the user's response to the second question.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method for receiving and processing patient medical information in a multiple server environment, comprising:
   (1) transmitting data comprising a question designed to obtain medical information by a first server selected from a plurality of servers to an application server, each of the servers storing the question data;
   (2) receiving data by a second server comprising a response to the question from the application server, the second server comprising the first server or another one of the plurality of servers;
   (3) analyzing the response data and codifying the response data with one or more code values using the second server; and
   (4) transmitting the codified response data by the second server to the application server;

wherein the application server is configured to interface with at least one of a storage device and an end user computer, the at least one of the storage device and the end user computer configured to retain interview state data related to the data comprising the question, the response data, and the codified response data and to not transmit the interview state to any of the plurality of servers.

2. A method according to claim 1, wherein the code values comprise interface terminology codes.

3. A method according to claim 1, wherein, between steps (1) and (2), the application server formats the data comprising a question, transmits the formatted data to the end user computer system, and receives a response to the question from the end user computer system.

4. A method according to claim 1, wherein the analyzing step comprises determining a next question to transmit to the application server.

5. A method according to claim 4, wherein steps (1) through (4) are repeated for the next question.

6. A method according to claim 1, wherein, between steps (3) and (4), the codified response data is formatted for integration with an electronic health record.

7. A method according to claim 6, wherein the formatting comprises formatting the analyzed data according to a Continuity of Care Document or a Clinical Document Architecture standard.

8. A method for a first computer system to receive and process patient medical information in a stateless manner with interview history state data including answers to questions, comprising:
   receiving, by the first computer system, an XML data file from a second computer system, the XML data file including patient interview history data;
   transmitting a first question from the first computer system to the second computer system by revising or rewriting the XML data file;
   receiving, by the first computer system, a further revised or rewritten XML data file, data in the further revised or rewritten XML data file comprising the patient interview history data along with data representing an answer to the first question from the second computer system; and
   analyzing, using the first computer system, the further revised or rewritten XML data file and adding data including one or more code values codifying the data representing an answer to create a still further revised or rewritten XML data file;
   wherein none of the XML data file, the revised or rewritten XML data file, the further revised or rewritten XML data file, or the still further revised or rewritten XML data file includes patient identifying data.

9. A method according to claim 8, further comprising retaining the patient identifying data on the second computer system.

10. A method according to claim 8, further comprising retaining the patient identifying data on a third computer system, the third computer system comprising the system initially transmitting data representing the answer to the first question to the second computer system.

11. A method according to claim 8, further comprising formatting at least some of the still further revised or rewritten XML data file for integration with an electronic health record.

12. A method according to claim 11, wherein the formatting comprises formatting the data according to a Continuity of Care Document or a Clinical Document Architecture standard.

13. A method according to claim 8, further comprising:
   retaining the patient identifying data on either the second computer system or a third computer system, the third computer system comprising the system initially transmitting data representing the answer to the first question to the second computer system;
   wherein the patient identifying data is stored temporarily in a non-transient computer readable medium.

14. A method according to claim 8, further comprising:
   retaining the patient identifying data on either the second computer system or a third computer system, the third computer system comprising the system initially transmitting data representing the answer to the first question to the second computer system;
   wherein the patient identifying data is stored in a database or in memory.

15. A system for receiving and processing patient medical information, comprising:
   a first computer system configured to transmit question data, receive answer data, codify the answer data, and transmit the answer data;
   the first computer system including a processor configured to execute a software as a service application configured to communicate with a middle tier application server and to transmit the question data and answer data; and
   a second computer system remote from the first computer system, the second computer system including or in communication with a non-transient computer readable medium configured to store patient identifying data related to the question and answer data,
   wherein the first computer system is configured to not store patient identifying data related to the question and answer data.

16. A system according to claim 15, wherein the application is configured to analyze answer data and determine a next question to transmit to the middle tier application server.

17. A system according to claim 15, further comprising a data file of interface terminology codes in communication with the application in order to codify the answer data.

18. A system according to claim 15, wherein the second computer system is the middle tier application server.

19. A system according to claim 15, wherein the second computer system is a computer system that generates the answer data in response to a user input and transmits the answer data to the middle tier application server.

20. A system according to claim 15, wherein the patient identifying data is stored temporarily in the non-transient computer readable medium.

21. A system according to claim 15, wherein the non-transient computer readable medium includes a database or memory.

* * * * *